United States Patent [19]

Albisetti et al.

[11] Patent Number: 4,931,551

[45] Date of Patent: Jun. 5, 1990

[54] DISPERSIONS OF CHITIN AND PRODUCT THEREFROM

[75] Inventors: Charles J. Albisetti, Rehoboth; John E. Castle, Lewes, both of Del.

[73] Assignee: University of Delaware, Newark, Del.

[21] Appl. No.: 214,977

[22] Filed: Jul. 5, 1988

[51] Int. Cl.$^5$ .................. C08B 37/00; C07H 5/00; A61K 31/00; D21D 1/00

[52] U.S. Cl. .................. 536/20; 536/55.3; 514/55; 162/158; 424/443; 424/445

[58] Field of Search .................. 536/20, 55.3; 424/445, 424/443; 162/158; 514/55

[56] References Cited

U.S. PATENT DOCUMENTS

| | | | |
|---|---|---|---|
| 2,978,446 | 4/1961 | Battista et al. | 260/212 |
| 3,847,897 | 11/1974 | Dunn et al. | 260/211 |
| 3,903,268 | 9/1975 | Balassa | 424/180 |
| 3,914,413 | 10/1975 | Balassa | 424/180 |
| 4,034,121 | 7/1977 | Dunn et al. | 426/565 |
| 4,056,432 | 11/1977 | Slagel et al. | 162/168.3 |
| 4,062,921 | 12/1977 | Austin | 264/233 |
| 4,286,087 | 8/1981 | Austin et al. | 536/20 |
| 4,392,916 | 7/1983 | Nishiyama et al. | 162/158 |
| 4,405,324 | 9/1983 | Cruz, Jr. | 424/443 |
| 4,532,321 | 7/1985 | Castle et al. | 536/20 |
| 4,651,725 | 3/1987 | Kifune et al. | 128/156 |
| 4,695,465 | 9/1987 | Kigasawa et al. | 424/445 |
| 4,699,135 | 10/1987 | Motosugi et al. | 128/156 |

FOREIGN PATENT DOCUMENTS

| | | | |
|---|---|---|---|
| 515424 | 8/1955 | Canada | 536/57 |
| 731639 | 4/1966 | Canada | 536/57 |
| 2505305 | 8/1975 | Fed. Rep. of Germany | |
| 61-174227 | 8/1986 | Japan | |
| 2182560 | 5/1987 | United Kingdom | |
| 2188135 | 9/1987 | United Kingdom | |

OTHER PUBLICATIONS

Julius Grant, Hackh's Chemical Dictionary, 1972, 4th Ed., p. 498.

Yalpani, "Chitin in Nature and Technology", pp. 403–406, Plenum Press, New York, N.Y. (1986).

Balassa et al., "Proceedings of the First International Conference on Chitin/Chitosan," MIT Sea Grant Report MITSG 78-7, pp. 296–305.

Primary Examiner—Ronald W. Griffin
Assistant Examiner—Everett White
Attorney, Agent, or Firm—Dean R. Rexford

[57] ABSTRACT

Ground chitin is rendered dispersible in aqueous medium to form stable dispersions on mild shearing, by pretreating the chitin with an aqueous oxidizing bleach solution. the dispersions, and paper-like structures prepared from them by papermaking techniques, are useful for treating and binding wounds.

Operable bleaches include peroxygen bleaches and labile halogen bleaches. Peroxygen bleaches include hydrogen and alkali metal peroxide, alkaline earth and alkali metal perborate, percarbonate, peroxymonosulfate, and bromate. The labile halogen bleaches include alkali metal and alkaline earth hypohalites, and dihalo-s-triazinetriones.

12 Claims, No Drawings

DISPERSIONS OF CHITIN AND PRODUCT THEREFROM

The Government of the United States of America has rights in this invention pursuant to Grant No. NA8-3AA-D-00017 awarded by the U.S. Department of Commerce.

BACKGROUND OF THE INVENTION

1. Field of the Invention

The invention is in the field of chitin dispersions useful in the treatment of wounds as dispersions per se and as certain other products such as paper-like structures which result from the coalescence of chitin in said dispersions.

2. Background and Description of the Prior Art

Chitin is a widely distributed polysaccharide occurring as the structural compound in the form of alpha chitin in the exoskeletons of such crustaceans as shrimp, krill, crabs, and lobsters and in the form of beta chitin in the internal pens of squid. Chitin occurs also in the exoskeletons of some insects and in the cell walls of some fungi. Indeed, chitin is second only to cellulose in tonnage of available natural polymers.

The repeating unit of the chitin polymer is 2-N-acetylglucosamine wherein a small fraction of the amino groups are unacetylated.

Chitin and its derivatives, especially deacetylated chitin, so-called chitosan, and derivatives, are finding increasing use as wound healing adjuvants, metal ion scavengers, waste water treatment and food processing compounds, and cosmetic aids.

A major deterrent to the wider use of chitin per se is its intractability. Chitin is modestly soluble in a few uncommon solvents. For example, Capozza in German Pat. No. 2,505,305 reported solubility in hexafluoroisopropanol, hexafluoroacetone, and its sesquihydrate. Austin in U.S. Pat. No. 4,062,921 employed dimethylacetamide or N-methylpyrrolidone containing several percent of lithium chloride to dissolve chitin and Balassa et al applied the classical viscose/xanthate process to chitin, as reported in MIT Sea Grant Report, MIT SG 78-7, p.296.

Dispersions of microcrystalline chitin have been prepared, albeit at the expense of significant hydrolytic degradation of the polymer chain, through pretreatment with hot strong acids, as reported, for example, by Dunn et al in U.S. Pat. Nos. 3,847,897 and 4,034,121, Austin et al in U.S. Pat. No. 4,286,087 and Castle et al in U.S. Pat. No. 4,532,321. Yalpani in "Chitin in Nature and Technology", Plenum Press, New York, N.Y. (1986) teaches dispersions of chitin prepared by extensive high pressure shearing, for example, 3 to 40 passes through a high energy mill at pressures of 4,000 to 15,000 psi (281 to 1055 kg/cm$^2$).

Sagar et al in British Pat. Nos. 2,182,560 and 2,188,135 teach the preparation of wound dressings, inter alia, by pouring a slurry of washed fungal mycelia into molds or onto a continuous paper-making apparatus, and freeze-drying the resultant mat. The mycelia are bleached before employment in a wet bandage.

SUMMARY OF THE INVENTION

In the process of dispersing chitin in aqueous medium by shearing, the improvement comprising pretreating said chitin with an oxidizing bleach selected from one of the groups of peroxygen bleaches and labile halogen bleaches the group of peroxygen bleaches consisting of hydrogen and alkali metal peroxide, alkaline earth and alkali metal perborate, percarbonate, peroxymonosulfate, persulfate, bromate; and the group of labile halogen bleaches consisting of alkali metal and alkaline earth hypohalite and dihalo-s-triazinetriones, whereby said chitin is rendered dispersible by mild shearing to form stable dispersions.

The dispersions form paper-like structures, hereinafter referred to as papers, when subjected to conventional paper-making processes or on simple drying on a substrate, for example on a plate according to the process taught by Battista et al in U.S. Pat. No. 2,978,446 for microcrystalline cellulose. As used in claims, the term 'coalescing' is taken to mean a process in which chitin in dispersion is separated from the aqueous medium by evaporation or by filtration or both and the chitin particles come together. The papers, as well as substrates treated with said dispersions, such as bandages or other wound dressings, are thought to be useful in accelerating wound healing, as taught by Balassa in U.S. Pat. No. 3,903,268. The labile halogen bleaches introduce halogen into the chitin molecule, possibly conferring antiseptic properties on the chitin.

DESCRIPTION OF THE PREFERRED EMBODIMENTS

The invention is readily carried out by the artisan using easily available materials. Commercial oxidizing bleaches are operable, i.e. those selected from the group consisting of hydrogen or alkali metal peroxides, alkaline earths and alkali metal perborates, percarbonates, peroxymonosulfates, persulfates, bromates, hypohalites, and the dihalo-s-triazinetriones. Those preferred are hydrogen peroxide, sodium hypochlorite, sodium perborate, sodium percarbonate, sodium peroxymonosulfate, potassium and sodium persulfate, sodium bromate, and sodium dichloro-s-triazinetrion. Most preferred is hydrogen peroxide.

The bleaches of the invention are those which are operable at room temperature or slightly above, say from about 15 deg. C. to about 50 deg. C. When those bleaches containing labile halogen such as the hypohalites are employed, the end product may contain halogen. This comes about because chitin contains acetamido and amino groups which are readily halogenated. The molecular weight of the product may also be reduced, whereas the molecular weight of invention products treated with peroxygen bleaches are essentially unchanged.

The pH of the reaction medium is not critical, although there are some preferred conditions, as the artisan will recognize. For example aqueous hydrogen peroxide per se is a sluggish bleach; raising the pH to about 11.5 increases the reaction rate so as to make it practical for use at room temperature. Near the other end of the pH scale, aqueous sodium monoperoxysulfate has a pH of about 4.0 and is readily operable at this pH at room temperature.

The artisan will select a suitable concentration of bleach by experiment to accommodate to the purity of the chitin which varies with the source of the chitin and the method of isolation. Commercial chitin may contain impurities such as proteins, lipids, colorants and the like which consume at least some of the bleach. As a rule, concentrations of from 1–5% by weight of bleach in water are employed, although more or less may be used as required.

The mechanism by which the chitin is so changed as to become readily dispersible is unknown. As demonstrated in examples, substantial reduction in molecular weight is not, in all cases, a precondition for ready dispersibility, as in the art.

The term 'mild shearing' as used in claims, means shearing conditions considerably milder than those taught by Yalpani supra. Illustrative of the degree of shearing taught in this application is the shearing provided by a simple blender, similar to those often seen in household kitchens, comprising an open atmospheric pressure container having at the bottom a simple propeller-like device capable of turning at say 20,000 rpm. Such a device is referred to infra as a 20,000 rpm blender and the process as mild shearing. The art device employed by Yalpani supra, is a laboratory homogenizer Model 15M (Gaulin Corporation), which pumps the slurry repeatedly through a mill at high pressure, thus providing much more severe shearing.

The dispersions of the invention, upon drying, coalesce forming paper-like structures. The papers vary in appearance from that of coarse filter paper to parchment in the case of beta chitin. Additives may be employed to modify the properties of the papers. Such additives, normally added to the dispersions, comprise softeners and humectants such as those often added to cellulose papers. Examples of useful additives are glycerine, ethylene glycol, and N-acetylethanolamine. Although the dispersions are remarkably stable, as set out in examples, stabilizers such as carboxymethyl cellulose and polyvinyl alcohol can be employed to further stabilize the dispersions for special purposes. Other materials, for example fibrous materials can be added for special effects. Such materials comprise, for example, cellulose pulps, ground cellulose, glass fibers, polyester fibrils and the like.

Although flat, i.e. planar, papers are described in examples it is within the invention to prepared shaped papers, for example, papers formed to fit a body part such as a heel. Such a procedure is within the skill of the artisan who might pour a dispersion into a porous mold much as clay slip is poured into porous plaster of Paris molds to prepare so-called 'green' hollow ceramic articles.

EXAMPLES

The chitin employed in the following examples came from several sources, as follows:

Alpha chitin:

Dungeness crab (*Cancer magistus*) obtained commercially from Protan, Inc., Redmond, Wash.

Tanner/Snow Crab (*Chionectes bairdi*) obtained commercially from Bioshell Corp., Albany, Oreg.

Blue Crab (*Callineactes sapidus*) obtained from the Chesapeake Bay. Work up was carried out in the usual manner (See Zikakis ed. Chitin, Chitosan and Related Enzymes, Academic Press, Inc. Orlando, Fla. (1984) p.xviii).

Beta chitin:

Squid (Loligo species) obtained from the North Atlantic Ocean. Work up was as above, except that the decalcification procedure was omitted as unnecessary.

Chitin, regardless of source, was ground to the mesh stated in examples.

Hydrogen peroxide, 3% was of pharmaceutical grade and sodium hypochlorite was a commercial preparation such as is used in home laundries. Other chemicals were chemically pure materials purchased in the laboratory chemicals trade.

Molecular weights were determined by intrinsic viscosity using a N,N-dimethylacetamide/5% lithium chloride solvent mixture and Mark-Houwink constants according to the method of Susan H. Sennett, Thesis, University of Delaware, June 1985.

Examples demonstrate the use of the preferred bleaches, i.e. hydrogen peroxide, sodium percarbonate, sodium borate, sodium peroxymonosulfate, sodium hypochlorite, and sodium dichloro-s-triazinetrione.

EXAMPLE 1

This example demonstrates a process of the invention wherein hydrogen peroxide is applied in a preliminary bleaching step at autogenous pH to oxidize adventitious impurities, followed by more severe treatment with hydrogen peroxide at pH 11.5 to render the chitin dispersible.

Alpha chitin from Dungeness crab, 15 g., 20 mesh, was stirred overnight at room temperature with 300 ml of 3% hydrogen peroxide. The chitin was filtered and washed with four 250 ml portions of distilled water. The wet filter cake was suspended in 750 ml of 1% hydrogen peroxide and the pH of the mixture was adjusted to 11.5 by dropwise addition of 50% sodium hydroxide. The mixture was stirred overnight at room temperature, filtered, and the filter cake was washed with five 2000 ml portions of distilled water.

The filter cake, after pressing on the filter to remove excess water, was suspended in 400 ml of distilled water and blended for 15 minutes in a 20,000 rpm blender. The resulting creamy dispersion contained about 3.75 wt. % solids and showed no appreciable syneresis after seven months.

A portion of the dispersion, when spread on a stainless steel plate and allowed to dry under room conditions, yielded a paper having the appearance of coarse filter paper.

EXAMPLE 2

This example illustrates the process of Example 1 applied to alpha chitin derived from Tanner crab. The yield was about 90%. Fifteen minute blending, as in Example 1, of a mixture of 3 wt. % treated chitin in water yielded a colorless dispersion showing no syneresis after one year.

EXAMPLE 3

This example illustrates a procedure avoiding the preliminary bleaching step of Examples 1 and 2.

Dungeness crab alpha chitin, 10 g., 40 mesh, was suspended in 200 ml. of 3% hydrogen peroxide and the pH of the mixture was adjusted to 11.5 by dropwise addition of 20% sodium hydroxide. The mixture was stirred overnight at 17 deg. C. and the fluffy white product was separated by filtration from a pale yellow filtrate. The filter cake, after washing with water, was added to fresh water to yield a 1% mixture which was blended as in Example 1. The resulting dispersion showed 2-3 wt. % syneresis after three months standing.

The molecular weight of two preparations was found to be $6.37 \times 10^5$ and $6.79 \times 10^5$. The starting material had a molecular weight, as measured by the same method, of $6.44 \times 10^5$.

EXAMPLE 4

This example illustrates the preparation of an invention dispersion using hydrogen peroxide and beta chitin from squid pens, the preparation of a paper from the dispersion, and the use of an additive for softening the paper.

Beta chitin from squid pens, 7.5 g., 20 mesh, was added to 150 ml. of 3% hydrogen peroxide previously adjusted to pH 11.5 by dropwise addition of 50 wt. % sodium hydroxide, and the mixture was stirred overnight.

Although the product appeared gelatinous, it was readily filtered. It was washed with water until the filtrate was neutral. The washed product (2.5 wt. %) was blended in 300 ml. of fresh water, as in Example 1, to yield a dispersion which was stable for at least four months.

On drying a portion of the dispersion on a flat plate, a parchmentlike paper formed which was reminiscent of the original squid pens. In a second experiment, an amount of bis-(2-hydroxyethyl) ether equal to about 8 wt. % of the chitin, was added to a portion of the dispersion. On drying, a softer paper was produced.

The molecular weight of the starting beta chitin was $3.2 \times 10^6$; after processing, the molecular weight was found to be essentially unchanged i.e. $1.41 \times 10^6$.

EXAMPLE 5

This example illustrates the use of sodium perborate tetrahydrate as a bleach in the invention process applied to alpha chitin.

Alpha chitin from Dungeness crab, 10 g., 40 mesh, was suspended in 200 ml. of water containing 10 g. of sodium perborate tetrahydrate. The initial pH was 11. The mixture was stirred overnight at 35 deg. C.

The product, after separation by filtration, was washed with fresh water until the filtrate was neutral. The product was blended in 250 ml of water as in Example 1. The dispersion containing about 4 wt. % solids, was stable for at least four months at room temperature.

EXAMPLE 6

This example illustrates the use of sodium percarbonate as a bleach in the treatment of alpha chitin according to the invention.

Alpha chitin from Dungeness crab, 10 g., 20 mesh, was suspended in 300 ml. of water containing 10 g. of sodium percarbonate (perhydrate). The mixture was stirred overnight at 35 deg. C. The product was filtered and rinsed four times on the funnel with 300 ml. portions of water. The filter cake resembled table salt. The product was dispersed as in Example 1 in 350 ml. of water to yield a thick creamy and stable dispersion. Drying of the dispersion on a plate yielded a paper.

EXAMPLE 7

This example illustrates the use of sodium perborate tetrahydrate as a bleach in the treatment of alpha chitin according to the invention.

Alpha chitin from Blue crab, 10 g., 40 mesh, was added to a solution of 10 g. sodium perborate tetrahydrate in 300 ml. water and the mixture was stirred overnight at 34 deg. C. The product was filtered and repeatedly washed on the funnel. The wet filter cake was dispersed in 320 ml. water as in Example 1 to produce a creamy dispersion containing about 3 wt. % solids. The dispersion, slightly off white, yielded a coarse paper on drying on a plate.

EXAMPLE 8

This example illustrates the use of potassium peroxymonosulfate as a bleach in the treatment of alpha chitin according to the invention.

A mixture of 10 g. of 40 mesh alpha chitin from Dungeness crab, 10 g. of potassium peroxymonosulfate and 200 ml. of water were stirred overnight at 36 deg. C. The initial pH of the mixture was 4. The product was filtered and washed four times on the funnel with 200 ml. portions of water. The filter cake was blended as in Example 1. The creamy white dispersion containing 3.3 wt. % solids was stable for at least four months. The dispersion on drying on a plate yielded a paper.

EXAMPLE 9

This example illustrates the use of sodium hypochlorite as a bleach in the treatment of alpha chitin according to the invention. It is shown that active chlorine is apparently introduced into the chitin molecule and the molecule is so modified that the product is no longer soluble in dimethylacetamide/lithium chloride.

Alpha chitin from Dungeness crab, 20 g., 20 mesh, was added to a room temperature mixture of 100 ml. of water and 100 ml. 5% sodium hypochlorite household bleach. Reaction occurred at once with foaming, gas evolution and bleaching of the chitin. The product was filtered and washed once with 1.4 l. of water and thereafter resuspended three times in 900 ml. of fresh water with intermediate centrifuging.

The washed product was blended in 150 ml. of water as in Example 1. The thick creamy dispersion had the odor of free chlorine. The dispersion was stable for at least seven months. On drying on a plate, a white paper was formed. The presence of free chlorine was established through the liberation of iodine from potassium iodide.

EXAMPLE 10

This example demonstrates the use of sodium dichloro-s-triazinetrione as bleach in the treatment of alpha chitin from Dungeness crab.

Alpha chitin from Dungeness crab, 10 g., 20 mesh, was suspended in 300 ml. of water containing 10 grams of sodium dichloro-s-triazinetrione. The mixture was stirred overnight at 36 deg. C. The product was filtered and washed with four 300 ml. portions of water. The wet filter cake was blended in 300 ml. of water as in Example 1. The creamy white dispersion had a chlorine odor and formed a paper on drying on a glass plate. The molecular weight was determined to be $1.77 \times 10^5$.

EXAMPLE 11

This example demonstrates the preparation of chitin papers by allowing dispersions of the invention to dry on a porous substrate in a manner simulating commercial paper making wherein dispersoids are taken up on screens and thereafter dried.

Although it is not critical to do so, dispersions are preferably diluted to about 0.5 wt. % solids before depositing the dispersed chitin on the porous substrate, preferably by applying suction to the bottom side. The porous substrate may be a fine screen, for example, or unglazed porcelain. Preferably the wet mats are removed from the substrate before drying them, for example, by allowing them to dry under room conditions.

Other means may, of course, be employed. Various solid additives, preferably fibrous materials, can be added to modify the properties of the papers.

Papers need not be planar. It is within the invention to fabricate papers of other shapes by, for example, employing porous molds of suitable shapes. For example, papers can be prepared to fit body parts such as an ankle.

Table 1 shows the effects of several additives on the paper product.

TABLE 1

| Dispersion, Ex. No. | Fibrous Additive | Ratio (wt.) Chitin/Additive | Product appearance |
| --- | --- | --- | --- |
| 4 | none | — | parchment |
| 6 | none | — | coarse filter paper |
| 1 | glass fiber pulp | 7/3 | smooth slick paper |
| 1 | same | 1/3 | slick creaseable paper |
| 1 | wood filter paper pulp | 7/3 | rough flexible paper |
| 1 | Hardwood dissolving pulp | 2/1 | flexible paper |
| 9 | same | 2/1 | bright white flexible paper |

EXAMPLE 12

This example demonstrates one use of the dispersions of the invention in the preparation of wound dressings. Dispersions prepared under Examples 1, 2, 4, 8, and 9 were spread on 4 in. (10.2 cm.) square prewetted commercial wound dressing pads by means of a glass rod. The dressing containing the dispersion of Example 8 was found after drying to have taken up 0.32 g. of chitin. Naturally, one may add more or less chitin. The wet or dry dressing can be enclosed in a protective envelope and sterilized, e.g. by autoclaving, as is conventional in the art.

To summarize, it is within the skill of the art to employ the invention dispersions in several ways, for example:
1. The dispersion per se can be applied directly to the wound and thereafter the wound can be wrapped in conventional dressings or;
2. The dispersion can be applied to the dressing before applying the dressing to the wound, either moist or after drying or;
3. A paper of the invention, optionally containing one or more pharmaceutically acceptable additives, can be applied directly to the wound before applying a conventional dressing or the paper can be applied as a part of a dressing package. The paper and packet can be employed either wet or dry.

EXAMPLE 13

This example demonstrates the employment of several humectants. An amount of the below indicated conventional humectants equal to 10% of the solids was mixed with selected dispersions of Examples. The mixtures were spread on flat stainless steel plates and allowed to dry, thereby forming papers according to the invention. The results are shown in Table 2 following.

TABLE 2

| Expt. No. | Dispersion Example No. | Humectant | Product Description |
| --- | --- | --- | --- |
| 1 | 7 | none | hard paper |
| 2 | 7 | N-acetylethanolamine | soft paper |
| 3 | 7 | bis-(2-hydroxyethyl)ether | intermediate between 1 and 2 |
| 4 | 7 | glycerine | soft paper |
| 5 | 4 | none | flexible translucent paper |
| 6 | 4 | N-acetylethanolamine | softer than 5 |
| 7 | 4 | bis-(2-hydroxyethyl)ether | flexible, soft paper |
| 8 | 4 | glycerine | slightly harder than 7 |
| 9 | 8 | none | hard paper, low tear strength |
| 10 | 8 | N-acetylethanolamine | softer than 9, stronger |
| 11 | 8 | bis-(2-hydroxyethyl)ether | softness between 9 and 10 |
| 12 | 8 | glycerine | hard paper, much thicker |

EXAMPLE 14

Comparative

This example demonstrates that unbleached chitin cannot, outside the invention, be dispersed to form stable emulsions on mild shearing.

The experiment of Example 6 was repeated with the change that sodium percarbonate bleach was not employed. When chitin of the same batch was suspended in water and blended as in Example 1, the product resembled a puree containing visible particles. It began almost immediately to flocculate.

Having now described our invention, we claim:

1. The dispersion resulting from mild shearing in aqueous medium of chitin pretreated with an aqueous oxidizing bleach.

2. The dispersion of claim 1 wherein said oxidizing bleach is selected from the group consisting of hydrogen, alkaline earth and alkali metal peroxide, alkaline earth and alkali metal perborate, percarbonate, peroxymonosulfate, persulfate, bromate, hypohalite, and the dihalo-s-triazinetriones.

3. The dispersion of claim 1 wherein said oxidizing bleach is selected from the group consisting of hydrogen peroxide, sodium hypochlorite, sodium perborate, sodium percarbonate, sodium peroxymonosulfate, potassium and sodium persulfate, sodium bromate, and sodium dichloro-s-triazinetrione.

4. The dispersion of claim 1 wherein said bleach is hydrogen peroxide.

5. The dispersion of claim 1 containing a fibrous additive.

6. The dispersion of claim 5 wherein said additive is selected from the group consisting of glass fiber pulp and wood paper pulp.

7. The dispersion of claim 1 containing additionally a humectant.

8. The dispersion of claim 7 wherein said humectant is selected from the group consisting of N-acetylethanolamine, bis-(2-hydroxyethyl)ether and glycerine.

9. The paper resulting from coalescing and drying an aqueous dispersion of chitin formed by shearing in water chitin which has been treated with an aqueous oxidizing bleach.

10. The paper of claim 9 wherein said chitin has been pretreated with a bleach selected from the group consisting of hydrogen, alkaline earth and alkali metal peroxide, alkaline earth and alkali metal perborate, percarbonate, peroxymonosulfate, persulfate, bromate, hypohalite, and the dihalo-s-triazinetriones.

11. The paper of claim 9 wherein said chitin has been pretreated with a bleach selected from the group consisting of hydrogen peroxide, sodium hypochlorite, sodium perborate, sodium percarbonate, sodium peroxymonosulfate, potassium and sodium persulfate, sodium bromate, and sodium dichloro-s-triazinetrione.

12. The wet mat resulting from coalescing an aqueous dispersion of chitin formed by shearing in water chitin which has been treated with an aqueous oxidizing bleach.

* * * * *